United States Patent [19]

Hochschild

[11] 4,374,082
[45] Feb. 15, 1983

[54] METHOD FOR MAKING A PHARMACEUTICAL AND/OR NUTRITIONAL DOSAGE FORM

[76] Inventor: Richard Hochschild, 2915 Pebble Dr., Corona Del Mar, Calif. 92625

[21] Appl. No.: 293,782

[22] Filed: Aug. 18, 1981

[51] Int. Cl.³ .......................... B28B 19/00; B29B 1/02
[52] U.S. Cl. ...................................... 264/129; 264/15; 264/118; 264/143; 264/148; 264/157; 424/199
[58] Field of Search ................ 264/15, 118, 129, 140, 264/143, 148, 157; 424/199, 359

[56] References Cited

U.S. PATENT DOCUMENTS

| | | | |
|---|---|---|---|
| 3,148,123 | 9/1964 | Werner | 264/129 |
| 3,608,030 | 9/1971 | Tint | 264/129 |
| 3,646,894 | 3/1972 | Hasten et al. | 264/148 |
| 3,920,783 | 11/1975 | Hara et al. | 264/118 |
| 4,271,196 | 6/1981 | Schmidt | 424/199 |

*Primary Examiner*—Donald E. Czaja
*Assistant Examiner*—W. Thompson
*Attorney, Agent, or Firm*—Fischer, Tachner & Strauss

[57] ABSTRACT

A method for making a solid pharmaceutical and/or nutritional dosage form that is suitable for oral administration. A prescribed dosage of a pharmaceutical or active substance (including either or both of a vitamin and mineral) is mixed with a carrier or base material comprising cohesive lecithin granules or powder. The resulting combination is blended into a substantially homogeneous mixture having a plastic consistency that is characteristic of the lecithin. The mixture is then shaped into a desired solid form by a conventional technique, such as, for example, that including either extruding, molding, or rolling. The shaped form is then cut into a plurality of convenient, swallowable dosage units ready for packaging and distribution. The dosage units may be coated, so as to be provided with a finished appearance and resistance to moisture.

10 Claims, No Drawings

METHOD FOR MAKING A PHARMACEUTICAL AND/OR NUTRITIONAL DOSAGE FORM

BACKGROUND OF THE INVENTION

1. Field of the Invention

This invention relates to an inexpensive and reliable method of utilizing lecithin, which has a cohesive, plastic structure, for making a solid pharmaceutical and/or nutritional dosage form of the type that is suitable for oral administration.

2. Prior Art

Briefly, and in general terms, lecithin is a solid nutrient that is characterized by cohesive and plastic mechanical properties. As will be recognized by those skilled in the art, lecithin is composed of a combination of known phosphatides. In the past, lecithin has been taken orally by many persons as a nutritional supplement in the form of capsules, granules, or liquid. Moreover, lecithin has also been included, in relatively small quantities, in some vitamin tablets in combination with other vitamins and nutrients. What is more, lecithin has also been used as an emulsifier or dispersant, or as a release, antispattering, or browning agent in several food products, such as chocolate, margarine and shortening. Combined with drugs, in low proportions, lecithin has been used as an emulsifier and suspending agent. However, no application is known in which lecithin has been used as a base or carrier material for independently supporting, in solid form, a combination of vitamins and/or other pharmaceutical substances that is to be shaped into a swallowable dosage form.

Tablets and capsules comprise the most common orally administered pharmacological dosage forms. Contrasted to liquids and powders, tablets and capsules offer the advantage of convenience, while enabling a precise dosage to be measured. However, a significant disadvantage of tablets and capsules is that, in addition to one or more active ingredients, the user also receives undesirable, non-active, and often synthetic additives which are utilized during the manufacture of the tablets or capsules. The non-active additives are typically glidants (such as, for example, talc, magnesium stearate, or calcium stearate) which are used to promote flow of the mixture before forming; anti-sticking agents (such as, for example, paraffin, stearic acid, or soaps) to prevent the mixture from sticking to the tableting machine dies; lubricants (such as, for example, talc, magnesium stearate, or calcium stearate) to reduce friction during compression; diluents or fillers (such as, for example, di-calcium phosphate or various sugars) to increase bulk and to make the tablet of swallowable size; binders (such as, for example, ethylcellulose or corn starch) to mechanically hold the tablet together; disintegrants (such as, for example, corn starch, methylcellulose, or wood products) to promote disintegration of the tablets in the gastrointestinal tract.

Capsules are frequency characterized by the same or similar disadvantages that are inherent in the manufacture of tablets, as has been described above. That is, glidants, diluents, fillers, and other inactive substances may be added to the contents of the capsule. Moreover, the material which forms the capsule shell (which material typically consists of between 10% to 30% of the total capsule weight) is also an additive substance, the composition of which may include synthetic materials. By way of one example, the amount of vitamin E in a capsule thereof typically varies between approximately 15% to 75% of the capsule weight. The remaining weight of the vitamin E capsule generally consists of shell material and vegetable oil utilized for encapsulating purposes.

Some consumers object to the relatively large percentages of undesirable, inactive, and often synthetic ingredients incorporated within tablets and capsules. The adverse and undesirable effects that may be produced by the above-mentioned, inactive additives can be magnified, inasmuch as vitamin/mineral supplements in the form of conventional capsules, tablets, and the like, are frequently taken one or more times a day over long intervals of time (i.e. years).

SUMMARY OF THE INVENTION

Disclosed herein is a method for making a solid pharmaceutical dosage form of the type that is suitable for oral administration. The present method includes the steps of blending lecithin, a cohesive and plastic, solid nutrient with a prescribed amount of pharmaceutical powders and/or granules and shaping the resulting plastic mixture into one or more swallowable dosage units.

Accordingly, it is a primary object of the present invention to provide a method for manufacturing a solid pharmaceutical dosage form, whereby to obviate the step of tableting or encapsulating, as is otherwise common to most prior art methods of fabricating dosage forms.

It is an additional object of the present invention to overcome the need for adding undesirable additives that are typically associated with conventional tablets or capsules.

It is, therefore, yet an additional object of the present invention to provide both a quick and simple method for manufacturing various pharmaceuticals, especially vitamins, and the like, in relatively pure form.

It is a further object of the present invention to reduce the costs for manufacturing solid dosage forms relative to the manufacturing costs that are typically incurred during the production of conventional dosage units in the form of either tablets or capsules.

It is a still further object of the present invention to provide swallowable dosage forms that are suitable for oral administration and have a convenient or desirable shape.

DESCRIPTION OF THE PREFERRED EMBODIMENT

The present method for making a solid pharmaceutical and/or nutritional dosage form, which is suitable for oral administration, is now described. Initially, prescribed amounts of one or more active ingredients (which ingredients may be in the form of granules, powders, and, in small quantities, oily liquids) are identified for administration to a user in the form of an oral dose. The active ingredients are then combined with powdered or granulated lecithin, which, as will be known to those skilled in the art, is a solid nutrient that is characterized by the mechanical properties of cohesiveness and plasticity. The active ingredients are blended with the lecithin by any suitable process, and the resulting combination is kneaded into a homogeneous mixture having a plastic consistency. Lecithin is a nutrient and, therefore, can also be considered as an active substance. However, and in accordance with the present method, the lecithin is primarily used herein for its cohesive and plastic mechanical properties, which properties are retained when the lecithin is mixed with other active substances. Accordingly, by virtue of its cohesive and plastic characteristics, the function of lecithin in the present method is primarily that of acting as a base or carrier for the purpose of providing a deformable, solid structure for a dosage form that is suitable for oral administration. It is to be understood that the term "active substance" will subsequently be used herein to describe pharmaceutical and nutritional substances other than lecithin which are to be shaped into a solid dosage form.

The mixture of lecithin and active ingredients is shaped into any suitable mass. In accordance with one preferred embodiment of the present invention, a suitable shaping technique includes the step of extruding the plastic mass into one or more elongated rods. By way of example, a commercially available extruder that may be used herein for shaping the plastic mixture is Extruder Model 417 manufactured by Manley Company of Kansas City, Mo.

The extruded or otherwise formed shape is then sliced by a knife edge into small tablet or capsule-shaped units of uniform size and shape, depending upon the dosage of the active substance to be consumed by the user. The dosage units may be coated with any of a variety of tablet coating materials to minimize the penetration therein of moisture and to provide the unit with a finished appearance.

Because lecithin is hydroscopic, the production steps, as just described, should preferably be undertaken in a relatively dry atmosphere in order to minimize the acquisition of moisture.

Although the presently disclosed method permits most unwanted additives, except for some coating materials, to be eliminated from the dosage units, small percentages of certain additives may be necessary for fabricating a unit which is easily digestible. More particularly, relatively small quantities (typically between 1% to 3% by weight) of such additives as granulating agents and disintegrants may become necessary, depending upon the composition of the dosage units. However, natural substances, such as cellulose and defatted soy polysaccharides are available as suitable granulating agents and disintegrants.

In practice, the decision to include a granulating agent and/or disintegrant depends upon certain considerations. The blend of lecithin and active substances may become brittle (that is, lose its plasticity) if the proportion of lecithin relative to active substances is too low. Lecithin can form a relatively low percentage of the blend (i.e. sometimes as low as 20%), if the active substance is in granular rather than powder form. Thus, the blend may contain relatively more granular active substance per unit weight. Granulating agents are frequently employed in the production of granules by the well-known technique of wet granulation.

Pure lecithin in the size and shape of a commercially available tablet distintegrates too slowly in the digestive system for adequate absorption. When combined with soluble active ingredients, the disintegration time of the blend will often be sufficiently rapid, so as to eliminate the need for added disintegrants. However, when the percentage of lecithin in the blend is relatively high or, in the case of compositions which do not distintegrate quickly, a disintegrant should be added to the blend to enhance the speed of disintegration. By way of example, an available, suitable natural disintegrant is that known by the trademark AVICEL, manufactured by FMC Corporation.

It has been discovered that lecithin can be blended with relatively large amounts of virtually any vitamin, mineral, or pharmaceutical substance, while retaining its plastic mechanical characteristic. By way of example, it has been found that a blend of lecithin and active substances will retain its plastic characteristic when the weight of the active substances, in either powdered or granular form, is 2 to 4 times greater than the weight of lecithin. More particularly, blends have been produced which exhibit suitable plasticity even though the blend consisted of as much as 77%, by weight, of vitamins in granular form and only 23% of lecithin.

It has been found that the plasticity of the blend can be increased by the addition thereto of a relatively small amount of oil (e.g. such as, for example, vegetable oil), typically in the range of between 0.5% to 5%, by weight. The ability to maximize the plasticity of the blend is especially advantageous when lecithin forms a relatively small percentage thereof. Oil which is added to the blend to increase plasticity may also consist of an active additive substance. For example, both vitamin E and vitamin A (e.g. beta-carotene) are oily substances and may be utilized for the purpose of increasing the plasticity of the blend. Thus, the oily additive may enhance the plasticity of the blend while, at the same time, provide a particular nutritional value (such as in the case of vitamin E and/or vitamin A).

EXAMPLE

By way of one particular example, recited below are the processing steps for manufacturing a dosage form that is suitable for oral administration. Ascorbic acid (vitamin C), in granular form, is mixed in a dry atmosphere with granular or powdered lecithin and AVICEL according to the ratio 67% ascorbic acid; to 30% lecithin; to 39% AVICEL. The ingredients are placed into a suitable mixer, such as the Double Arm Mixer manufactured by Day Mixing Companying of Cincinnati, Ohio. The ingredients are thus mixed, blended and kneaded into a viscous, dough-like consistency. When the mix has attained the characteristic of a homogeneous dough, it is removed from the mixer and introduced into any one of a variety of available food or confectionary extruders (such as the extruder which has been identified above). The resulting blend is then extruded into a rod-like configuration, having a diameter of 0.220 inches. Knife blades are used to cut the rod into individual segments, each segment having a length of approximately ⅛ inches. The individual segments or units are then tumbled in a conventional revolving tablet coating and polishing pan within a dry, warm atmosphere, so as to round off the sharp corners thereof. The units, which have a dosage suitable for oral consumption, are now in a final form ready to be bottled or bulk packaged for distribution to a user.

As has been disclosed above, and in accordance with the present invention, it has been found that lecithin, a cohesive, plastic solid nutrient, can be loaded or mixed with proportionately large amounts of pharmaceutical powders and granules, such that the plastic characteristic of the resulting blend will be preserved. Thus, the lecithin functions as a base, carrier, or mechanical structure for retaining one or more active substances during the manufacture of a pharmaceutic and/or nutritional dosage form. The lecithin advantageously eliminates the need for the conventional capsule, which forms an external shell or skeleton. Therefore, and in accordance with the present method, lecithin may be considered as forming an inner skeleton for binding together various active substances, whereby to provide the resultant pharmaceutical dosage form with mechanical stability while permitting the form to be worked into a variety of commercially acceptable and swallowable shapes.

Lecithin, as used herein, offers the further advantage in that it provides the user with a nutritional supplement in addition to those active substances that are combined in the pharmaceutical dosage form. Yet another advantage of combining lecithin with the active substances to form a pharmaceutical dosage form is that lecithin is an antioxidant. Hence, lecithin functions as a preservative to thereby stabilize the active ingredients against breakdown caused by oxidation. Unesterified vitamin E also acts as an antioxidant, and, therefore, may be used in addition to the lecithin to further stabilize the dosage form, whenever appropriate.

It will be apparent that while a preferred embodiment of the invention has been shown and described, various modifications and changes may be made without departing from the true spirit and scope of the invention. It is to be recognized that lecithin is not necessarily the only substance which offers the cohesive and plastic properties that are essential to the production of a pharmaceutical form in accordance with the present method. However, few substances are known which advantageously have a nutritional value as well as the aforementioned mechanical characteristics that lend themselves to the formation and structure of the solid dosage form, as has been described above.

Having thus set forth a preferred embodiment of the present invention, what is claimed is:

1. A method other than tableting or encapsulating for making a dosage form suitable for oral administration, wherein lecithin, by way of the cohesive characteristics thereof, is utilized as a carrier or base by which active substances may be combined with the lecithin in a solid structure, said method comprising the steps of:
   blending one or more active substances with the lecithin,
   working the blend into a homogeneous mixture having a plastic consistency, and
   shaping said mixture into one or more swallowable dosage units.

2. The method recited in claim 1, including the additional step of coating the swallowable units with a moisture resistant material.

3. The method recited in claim 1, including the additional step of extruding said plastic mixture to form an elongated rod-like structure thereof prior to the step of shaping said mixture into swallowable units.

4. The method recited in claim 1, including the additional step of rolling said plastic mixture into an elongated rod-like structure thereof prior to the step of shaping said mixture into swallowable units.

5. The method recited in claim 1, including the additional step of cutting said plastic mixture into a plurality of pieces prior to the step of shaping said mixture into swallowable units.

6. The method recited in claim 1, including the additional step of granulating said pharmaceutical and/or nutritional substances, to thereby reduce the brittleness of said plastic mixture.

7. The method recited in claim 1, including the additional step of adding a disintegrant to said plastic mixture, to thereby minimize the time in which the dosage units disintegrate within the body.

8. The method recited in claim 1, including the additional step of adding an oily liquid to said plastic mixture, to thereby enhance the plasticity thereof.

9. The method recited in claim 1, wherein during said blending step, lecithin is added, so as to form at least 20% by weight of the dosage units.

10. The method recited in claim 1, including the additional step of shaping said swallowable dosage units by tumbling said units to round off the edges thereof.

* * * * *